United States Patent [19]

Sweeney

[11] Patent Number: 5,057,638
[45] Date of Patent: Oct. 15, 1991

[54] PROCESS FOR MAKING 1-HEXENE FROM 1-BUTENE

[75] Inventor: William A. Sweeney, Larkspur, Calif.

[73] Assignee: Chevron Research and Technology Company, San Francisco, Calif.

[21] Appl. No.: 542,386

[22] Filed: Jun. 22, 1990

[51] Int. Cl.$^5$ .................................................. C07C 1/00
[52] U.S. Cl. ...................................... 585/324; 585/510; 585/520; 585/639; 585/643; 585/644; 585/648; 585/653
[58] Field of Search ............... 585/324, 510, 520, 639, 585/643, 644, 648, 653

[56] References Cited

U.S. PATENT DOCUMENTS

| | | | |
|---|---|---|---|
| 3,283,027 | 11/1966 | Lundeen et al. | 260/682 |
| 3,595,920 | 7/1971 | Ellis et al. | 260/683 |
| 3,600,455 | 8/1971 | Dean | 260/682 |
| 4,234,752 | 11/1980 | Wa et al. | 585/640 |
| 4,490,567 | 12/1984 | Drake | 585/324 |

FOREIGN PATENT DOCUMENTS

| | | |
|---|---|---|
| 0222356 | 5/1987 | European Pat. Off. . |
| 0150832 | 2/1988 | European Pat. Off. . |
| 1233020 | 5/1971 | United Kingdom . |

OTHER PUBLICATIONS

Banks, *Chemtech*, Feb. 1986, pp. 112–117.
Lundeen, et al., *JORG Chem.*, vol. 32, 1967, pp. 3386–3389.
Davis, *American Chemical Society*, vol. 18, No. 3, 1979, pp. 1919–198.
Che, et al., *Elsevier Science Publishers* B.V., Amsterdam, 1985, pp. 309–318.

*Primary Examiner*—Curtis R. Davis
*Attorney, Agent, or Firm*—Richard J. Sheridan; Tom G. DeJonghe

[57] ABSTRACT

Disclosed is a process for preparing 1-hexene from 1-butene. The 1-butene is metathesized to produce 3-hexene which is then subjected to, e.g., an hydration/dehydration procedure to produce a mixture of n-hexenes containing 1-hexene.

18 Claims, No Drawings

PROCESS FOR MAKING 1-HEXENE FROM 1-BUTENE

BACKGROUND OF THE INVENTION

1. Field of the Invention

The present invention relates to a method for producing 1-hexene from 1-butene.

2. Description of the Prior Art

Compounds having a terminal double bond (hereinafter referred to as "terminal olefins" or "α-olefins") are very useful industrially as raw materials for heat-resistant polymers, comonomers for the production of polyolefins, starting materials for detergents and so forth. The terminal olefin 1-hexene is especially valuable for many uses such as dimerization to dodecenes which are suitable for making biodegradable detergents, using it as a feed for the OXO reaction to make relatively linear $C_7$ alcohols, and as a comonomer in making linear low density polyethylene.

A potential source of 1-hexene is a mixture of n-hexenes which contains 1-hexene, cis and trans 2-hexene, and cis and trans 3-hexene. Unfortunately, however, the amount of 1-hexene in these mixtures is normally very low. For example, thermodynamic equilibration of n-hexenes produces a mixture containing only about 2-4 percent 1-hexene. While it is possible to separate the 1-hexene from the other n-hexenes in these mixtures, due to the very low levels of 1-hexene such a procedure would be uneconomical. Thus, there exists a need for a process by which 1-hexene can be made economically and in useful quantities.

One method for obtaining n-hexenes is to convert 1-butene into 3-hexene by the well known metathesis reaction (also called a "dismutation" reaction) discussed by R. L. Banks in Chemtech, February 1986, p. 112. Ethylene is a co-product. The 3-hexene can be thermodynamically isomerized to an n-hexene mixture with acidic, basic or transition metal catalysts well known in the art. There are many references to the metathesis reaction; one reference, U.S. Pat. No. 3,595,920, issued July 21, 1971 to Alas et al., describes a silver-modified molybdenum oxide on alumina catalyst.

A known method for producing terminal olefins, such as 1-hexene, is to dehydrate a 2-alcohol, i.e., a compound of the formula

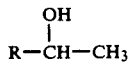

where R is a hydrocarbyl group. For example, U.S. Pat. No. 3,283,027, issued Nov. 1, 1966 to Lundeen et al., discloses the dehydration of 2-alcohols to terminal olefins (also known as "α-olefins") using a catalyst which is a thorium, scandium, yttrium or rare earth oxide. While this dehydration reaction can produce an α-olefin and/or a 2-olefin, the Lundeen et al., product is said to be 90% or more α-olefin.

U.S. Pat. No. 3,600,455, issued Aug. 17, 1971 to Dean, discloses a process for producing the terminal olefin 4-methyl pentene-1 by dehydrating 4-methyl pentanol-1 or 4-methylpentanol-2 by passing it over an alkalized alumina catalyst.

U.S. Pat. No. 4,234,752, issued Nov. 18, 1980 to Wu et al., discloses the dehydration of $C_{2-20}$ alcohols in the presence of gamma-alumina (which may be base-treated) employing an inert carrier gas to produce an olefin. The process is said to minimize isomerization which can convert desired products to undesired products. For example, according to Wu et al., 3-methyl-1-butanol can be dehydrated by this process to produce 3-methyl-1-butene having a 97.7 wt. % purity.

U.S. Pat. No. 4,490,567, issued Dec. 25, 1984 to Drake, discloses a process for the selective dehydration of 2-alcohols to α-olefins using a catalyst which is (1) at least one catalytic metal oxide on a low surface area aluminum oxide-containing support, or (2) a mixture of thorium oxide and cerium oxide on a base-treated aluminum oxide-containing support. Also described is a process for obtaining high purity 4-methyl-1-pentene by the dehydration of 4-methyl-2-pentanol followed by disproportionation with ethylene.

European Patent Specification Publication No. 0150832, published Nov. 2, 1988, discloses a process for preparing α-olefins by dehydrating 2-alcohols using a high purity (i.e., substantially free of silicon and titanium) zirconium oxide catalyst, and European Patent Specification Publication No. 0222356, published May 20, 1987, discloses the dehydration of 2-alcohols to α-olefins using a zirconia catalyst which has been treated with an alkaline solution.

Lundeen and Hoozer, "Selective Catalytic Dehydration. Thoria-Catalyzed Dehydration of Alcohols", J. Org, Chem., 32, pp. 3386–3389 (1967) discloses that the thoria-catalyzed dehydration of secondary 2-alcohols is selective for α-olefins, and that the amount of ketone by-product is low, and Davis, "Catalytic Conversion of Alcohols. 11. Influence of Preparation and Pretreatment on the Selectivity of Zirconia", Ind. Eng. Chem. Prod. Res. Dev., Vol. 18, No. 3, pp. 181–198 (1979) discloses that a zirconia catalyst is similar to thoria for both the dehydration and α-olefin selectivity in the conversion of 2-alcohols to olefins.

Other methods of preparing α-olefins are also known. For example, British Patent Specification No. 1,233,020, published May 26, 1971, discloses a method for making 4-methylpentene-1 by subjecting a mixture of acetone and isobutyraldehyde to conditions under which acetone undergoes condensation both with itself to form diacetone alcohol and with isobutyraldehyde to form the acetone/isobutyraldehyde condensate methyl, 2-methyl 3-hydroxy butyl ketone, subjecting the mixed condensates to conditions under which they undergo dehydration to the corresponding olefinically unsaturated ketones, hydrogenating these ketones to saturated alcohols and dehydrating these saturated alcohols over alkalized alumina to form a mixture of 4-methylpentenes-1 and −2 and a mixture of methylhexenes.

A process for producing 1-hexene has now been discovered which uses 1-butene, which is abundant and relatively inexpensive, as the starting material.

SUMMARY OF THE INVENTION

There is provided in accordance with the present invention, a process for making 1-hexene comprising:

A. metathesizing 1-butene to a mixture comprising 3-hexene and ethylene;

B. separating the 3-hexene from the product of step A;

C. reacting the 3-hexene with an electrophilic compound containing reactive hydrogen under acid catalyzed conditions which permit the electrophilic compound containing reactive hydrogen to add to carbon-carbon double bonds; and D. cracking the product of step C to produce a mixture of n-hexenes containing 1-hexene.

In accordance with the present invention, there is also provided a process for making 1-hexene comprising:
A. metathesizing-butene to a mixture comprising 3-hexene and ethylene;
B. separating the 3-hexene from the product of step A;
C. reacting the 3-hexene with an electrophilic compound containing reactive hydrogen under conditions which permit the electrophilic compound to add to carbon-carbon double bonds, said electrophilic compound being hydrolyzable to an alcohol after addition to the carbon-carbon double bond;
D. hydrolyzing the product of step C to produce of mixture of $C_6$ alcohols; and
E. cracking the product of step D to produce a mixture of n-hexenes containing 1-hexene.

The present invention further provides a process for making 1-hexene comprising:
A. metathesizing 1-butene to a mixture comprising 3-hexene and ethylene;
B. separating the 3-hexene from the product of step A;
C. reacting the 3-hexene with an electrophilic reactant selected from the group consisting of water and a hydrolyzable electrophilic compound containing reactive hydrogen under acid catalyzed conditions which permit the electrophilic reactant to add to carbon-carbon double bonds;
D. when the electrophilic reactant employed in step C is a hydrolyzable eleotrophilic compound containing reactive hydrogen, hydrolyzing the product of step C to from alcohols;
E. converting the alcohols produced to alkyl xanthates; and
F. cracking the product of step E to produce a mixture of n-hexenes containing 1-hexene.

There is further provided in accordance with this invention a process for making 1-hexene comprising:
A. metathesizing 1-butene to a mixture comprising 3-hexene and ethylene;
B. separating the 3-hexene from the product of step A;
C. reacting the 3-hexene with an electrophilic compound containing reactive hydrogen under conditions which permit the electrophilic compound containing reactive hydrogen to add to carbon-carbon double bonds;
D. cracking the product of step C to produce a mixture of 2-hexene and 3-hexene;
E. reacting the mixture of 2-hexene and 3-hexene produced in step D with an electrophilic compound containing reactive hydrogen under conditions which permit the electrophilic compound containing reactive hydrogen to add to carbon-carbon double bonds; and
F. cracking the product of step E to produce a mixture of n-hexenes containing 1-hexene.

DETAILED DESCRIPTION OF PREFERRED EMBODIMENTS

It would be expected that when an electrophilic compound containing reactive hydrogen is added to 3-hexene that the electrophilic compound would add to the double bond of the 3-hexene and form only the 3-hexyl isomer, i.e., the negative group of the electrophilic compound (e.g., —OH) would be on the third carbon atom of the hexyl chain. It would also be expected that this 3-hexyl isomer would not produce 1-hexene in a subsequent cracking step. Therefore, it appears that an isomerization step would be required to convert the 3-hexene into an n-hexene mixture containing some 2-hexene from which 1-hexene can be obtained.

The process of the present invention permits a more direct production of 1-hexene from 1-butene. This more direct production is achieved because, in a preferred embodiment of the invention, no 3-hexene isomerization step is required in the process of this invention.

In a preferred embodiment, the process of the present invention encompasses the use of an acidic catalyst when the electrophilic compound containing reactive hydrogen is reacted with the 3-hexene. (when an acid such as sulfuric acid is used as the electrophilic compound containing reactive hydrogen, no additional acid is required for catalysts). Quite surprisingly, the use of such a catalyst results in the production of some of the 2-isomer from which 1-hexene can be made directly.

In a less preferred, but still viable embodiment the process of the present invention does not employ an acidic catalyst when the electrophilic compound is reacted with the 3-hexene. In this case, no significant amount of 2-isomer will be formed directly from the 3-hexene. Thus, it is necessary to react the 3-hexene with the electrophilic compound containing reactive hydrogen, crack the resulting 3-isomer to produce a mixture of 2-hexene and 3-hexene, react this mixture again with the electrophilic compound containing reactive hydrogen to produce a mixture of 2-isomer and 3-isomer (e.g., 2-hexanol and 3-hexanol), and cracking the mixture of 2- and 3-isomers to produce a mixture of n-hexenes containing 1-hexene.

At the beginning of the process of this invention, 1-butene is fed into a typical metathesis process (such as that exemplified by the Phillips "Triolefin" process; see R. Streck, J. Mol. Cat., 1989, Vol. 46, p. 305). Typical catalysts used in the metathesis reaction are oxides of Cr, W, Mo and Re supported on alumina, silica and the like. Relatively high temperatures of 300°–400° C. may be employed, as in the Triolefin process. Alternatively, with high activity catalysts such as $Re/Al_2O_3$, mild conditions of about ambient temperature and pressure may be used. Other metathesis catalysts, both heterogeneous and homogeneous, are suitable for use in this invention.

In general, the catalyst and conditions are chosen to minimize olefin isomerization during metathesis since this results in the formation of $C_3$ and $C_5$ by-products. The catalyst and conditions described in the aforementioned U.S. Pat. No. 3,595,920, which is incorporated by reference herein in its entirety, are suitable. The silver-modified molybdenum oxide on alumina catalyst is used at an intermediate temperature of 100°–150° C. Partial conversion of about 30 to 70% is employed to minimize isomerization of the 3-hexene product with concomitant formation of $C_{7+}$ by-products. This procedure gives about 90% molar yield of hexene (comprising predominantly 3-hexene) from 1-butene.

When the 3-hexene has been separated from the metathesis reaction product, it is reacted with an electrophilic compound containing reactive hydrogen, preferably under acidic conditions. Examples of suitable electrophilic compounds containing reactive hydrogen include, but are not limited to, water carboxylic acids (such as formic acid acetic acid, trimethylacetic acid and dimethylacetic acids), and sulfuric acid. The electrophilic compound containing reactive hydrogen is reacted with the 3-hexene, under conditions which permit it to add to the carbon-carbon double bond in the 3-hexene, when the reaction conditions are acidic the resulting reaction product comprises a mixture of 2- and 3-hexyl isomers

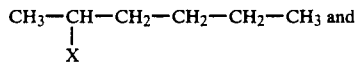

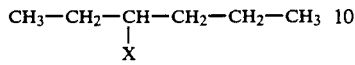

where X is the negative group (e.g., —OH, —OOCCH$_3$ or HSO$_4$—) from the electrophilic compound containing reactive hydrogen.

The conditions for the addition of the electrophilic compound to the olefins are well known in the art. Generally, acid catalysis is useful. This can often be provided by the electrophilic compound itself.

The electrophilic compounds containing reactive hydrogen useful in this invention fall into two general categories. The first category comprises compounds which, after they have added to the double bonds in the hexene isomers, can be removed directly by cracking the 2- and 3-hexyl isomers. Compounds which fall into this category include water and carboxylic acids, such as formic acid, acetic acid, trimethylacetic acid and dimethylbutyric acids. (In some cases, it may be desirable, though not necessary, to hydrolyze the electrophilic compounds in the first category, such as the carboxylic acids, to alcohols prior to cracking.) The second category of electrophilic compounds containing reactive hydrogens comprises compounds which add to the double bonds in the hexenes, but which are not readily removed from the 2- and 3-hexyl isomers by cracking, e.g., sulfuric acid. When this second category of compounds is used, the 2- and 3-hexyl isomers produced are subjected to an intermediate step, such as hydrolysis, to convert the negative group from the electrophilic compound containing reactive hydrogen (i.e., X in the above formulas) to a group, such as hydroxyl, which can be readily removed from the 2- and 3-hexyl isomers by cracking.

When the electrophilic compound containing reactive hydrogen employed is water, the 2- and 3- hexyl isomers produced will contain hydroxyl groups in the 2 and 3 positions, i.e., the product will contain 2-hexanol and 3-hexanol. Also, some of the electrophilic compounds containing reactive hydrogen which are useful in this invention ca be hydrolyzed to hydroxyl after addition to the double bond. These alcohols can be converted to xanthate groups, i.e , "2-xanthate" and "3-xanthate" compounds prepared, respectively, from 2-hexanol and 3-hexanol, which can then be removed via cracking. This conversion of alcohol to xanthate can be accomplished by reacting the alcohol with carbon disulfide (CS$_2$) in the presence of base (e.g., NaOH), followed by alkylation with, e.g., methyl iodide.

As stated above, the product of the reaction of the hexenes with the electrophilic compound containing reactive hydrogen is a mixture of 2- and 3-hexyl isomers. This mixture can be used in the subsequent cracking procedure as it is, or, alternatively, the 2-isomers (e.g., 2-hexanol) may be separated from the mixture of 2- and 3-isomers and only the 2-isomer subjected to cracking. By separating the isomers in this manner, the concentration of 1-hexene in the product of the cracking procedure will be maximized.

Once the 2- and 3-hexyl isomers produced by reaction of the 3-hexene with the electrophilic compound containing reactive hydrogen contains a group which is readily removed by cracking, the mixture of 2- and 3-hexyl isomers (or the 2-isomer alone) is cracked. Depending upon the particular readily removable group which is present on the 2- and/or 3-hexyl isomers, removal of the group may be accomplished by simple thermal cracking or by a cracking procedure which utilizes a catalyst. For example, when acetic acid is used as the electrophilic compound containing reactive hydrogen, thermal cracking may be used. When the 2- and 3-hexyl isomers are 2- and 3-hexyl alcohols, the cracking is preferably conducted in the presence of a mildly basic metal oxide catalyst, water is removed from each molecule to produce a mixture of 1-hexene, 2-hexene and 3-hexene.

The materials useful as cracking catalysts should not be acidic or strongly basic. Acid catalysts can isomerize the α-olefin product to internal olefins, which is undesirable. If a strongly basic catalyst is used appreciable dehydrogenation of the alcohol would occur, which is undesirable. Thus, suitable catalysts are mildly basic metal oxides which do not cause appreciable dehydrogenation of the alcohol and which exhibit selectivity for the production of α-olefins. While not specific to the production of 1-hexene, this general type of catalyst is discussed in an article by Burtron H. Davis entitled "Alcohol Conversion Selectivity as a Measure of the Base Strength of Metal Oxide Catalysts" in Che et al., *Adsorption and Catalysis on Oxide Surfaces* (1985); which article is incorporated by reference herein in its entirety Examples of mildly basic metal oxides suitable as catalysts in this invention include the oxides of Y, Zr, La, ln, Ce, Pr, Nd, Sm, En, Dy, Ho, Yb and Th.

It has been found that hydrous zirconium oxide prepared by a particular technique is an especially suitable catalyst. This catalyst is prepared by precipitating/digesting soluble ZrO(NO$_3$)$_2$ at high pH above room temperature (e.g., about 50°–75° C.), washing the resulting product thoroughly with both aqueous ammonia and water and drying exhaustively (e.g., at 80° C. or higher under vacuum for at least 16 hours). Before use, the catalyst is calcined at about 350°–650° C. This catalyst provides excellent conversion of 2-hexanol to olefin as well as excellent selectivity for α-olefin in the product.

The above-described process can be depicted by the following general reaction scheme. This general reaction scheme is illustrative only and is not intended to limit the present invention in any way.

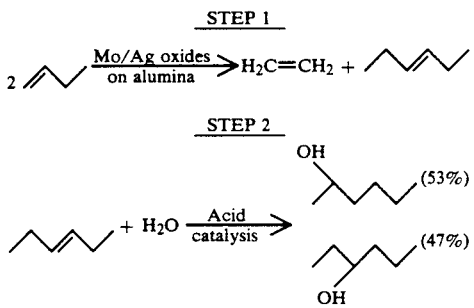

As described above, the 2-isomer is not expected from the simple, direct addition of an electrophilic compound containing reactive hydrogen to 3-hexene. However, when water, a simple electrophilic compound, is added to 3-hexene in the presence of an acid catalyst, both the 2- and 3-isomers are obtained.

The yield of 2-hexyl isomer (which ultimately can yield 1-hexene) in Step 2 (53 wt.% of the total product) is approximately equal to the yield which would be expected for random addition of the water to the internal carbon atoms, i.e., 50% of the alcohols produced would be expected to be 2-hydroxy hexane if random addition occurred. However, it has been found that the amount of 2-hexyl isomer can be increased significantly above this random level by using an electrophilic compound containing reactive hydrogen other than water. For instance, if acetic acid is used, the product contains about 63% of the 2-isomer and 37% of the 3-isomer. Using sulfuric acid as the electrophilic compound containing reactive hydrogen yields a product containing about 73% of the 2-isomer and 27% of the 3-isomer. The use of "bulky" acids, such as trimethyl acetic acid or dimethylbutyric acids' should likewise increase the amount of 2-isomer in the product.

The product of Step 2 can next be "cracked" to a mixture of n-hexenes which contains 1-hexene.

STEP 3

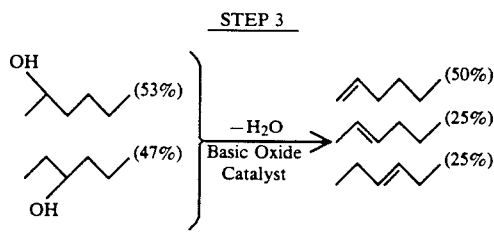

The desired product from the above reaction sequence is, of course, 1-hexene However, it is not necessary that the 1-hexene be separated from the 2- and 3-hexene in order for it to be useful. For example, the mixture of 1-, 2- and 3-hexene can be used as a starting material for the copolymerization of 1-hexene and ethylene. Since 2- and 3-hexene will not react to copolymerize with the ethylene, they act simply as an inert diluent which can be recovered following the copolymerization of the 1-hexene and ethylene. Thus, the copolymerization also serves as a means of separating the 2- and 3-hexene from the 1-hexene.

Should it be desirable to separate the 1-hexene from the mixture of 1-, 2- and 3-hexene prior to its use, this can be accomplished by techniques such as distillation or adsorption which are well known in the art.

The processes of the present invention may be conducted either as a batch process or in a continuous manner. It is generally preferable to conduct the process in a continuous manner. The product of the cracking step will generally contain some quantity of 2- and/or 3-hexenes, and possibly some compounds which were not cracked and still contain the electrophilic group of the electrophilic compound containing reactive hydrogen (e.g., alcohols). Thus, the processes of this invention are advantageously conducted by recovering the desired product, 1-hexene, from the product of the cracking step a nd recycling any remaining n-hexenes and uncracked compounds to be used as a portion of the feed for the reaction with the electrophilic compound containing active hydrogen. This may be accomplished by recycling these compounds to a point in the process before reaction with the electrophilic compound containing reactive hydrogen. In this way the amount of 1-hexene produced from a given mixture of $C_6$ olefin isomers is maximized.

One of the principle advantages of the present invention is that it provides a process whereby 1-hexene can be produced in commercially acceptable amounts from an abundant and inexpensive starting material, 1-butene.

What is claimed is:

1. A process for making 1-hexene comprising:
    A. metathesizing 1-butene to a mixture comprising 3-hexene and ethylene;
    B. separating the 3-hexene from the product of step A;
    C. reacting the 3-hexene with an electrophilic compound containing reactive hydrogen under acid catalyzed conditions which permit the electrophilic compound containing reactive hydrogen to add to carbon-carbon double bonds; and
    D. cracking the product of step C to produce a mixture of n-hexenes containing 1-hexene.

2. A process for making 1-hexene comprising:
    A. metathesizing 1-butene to a mixture comprising 3-hexene and ethylene;
    B. separating the 3-hexene from the product of step A;
    C. reacting the 3-hexene with an electrophilic compound containing reactive hydrogen under acid catalyzed conditions which permit the electrophilic compound containing reactive hydrogen to add to carbon-carbon double bonds;
    D. separating the 2-isomer produced in step C from the product of step C; and
    E. cracking said 2-isomer to produce a mixture of n-hexenes containing 1-hexene.

3. The process of claim 1 or 2 wherein the electrophilic compound is selected from the group consisting of water and carboxylic acids.

4. The process of claim 1 or 2 further comprising separating the 1-hexene from the product of the cracking step and recycling the remainder of said product to form a portion of the material used to react with the electrophilic compound containing reactive hydrogen.

5. A process for making 1-hexene comprising:
    A. metathesizing 1-butene to a mixture comprising 3-hexene and ethylene;
    B. separating the 3-hexene from the product of step A;
    C. reacting the 3-hexene with an electrophilic compound containing reactive hydrogen under conditions which permit the electrophilic compound to add to carbon-carbon double bonds, said electrophilic compound being hydrolyzable to an alcohol after addition to the carbon-carbon double bond;
    D. hydrolyzing the product of step C to produce of mixture of $C_6$ alcohols; and
    E. cracking the product of step D to produce a mixture of n-hexenes containing 1-hexene 6. A process for making 1-hexene comprising:
    A. metathesizing 1-butene to a mixture comprising 3-hexene and ethylene;
    B. separating the 3-hexene from the product of step A;
    C. reacting the 3-hexene with an electrophilic compound containing reactive hydrogen under conditions which permit the electrophilic compound to add to carbon-carbon double bonds, said electrophilic compound being hydrolyzable to an alcohol after addition to the carbon-carbon double bond;

D. hydrolyzing the product of step C to produce of mixture of $C_6$ alcohols;

E. separating 2-hexanol from the mixture of $C_6$ alcohols produced in step D; and F. cracking the 2-hexanol to produce a mixture of n-hexenes containing 1-hexene 7. The process of claim 5 or 6 further comprising separating the 1-hexene from the product of the cracking step and recycling the remainder of said product to form a portion of the material used to react with the electrophilic compound.

8. The process of claim 5 or 6 wherein the electrophilic compound is sulfuric acid or a carboxylic acid.

9. A process for making 1-hexene comprising:
A. metathesizing 1-butene to a mixture comprising 3-hexene and ethylene;
B. separating the 3-hexene from the product of step A;
C. reacting the 3-hexene with an electrophilic reactant selected from the group consisting of water and a hydrolyzable electrophilic compound containing reactive hydrogen under acid catalyzed conditions which permit the electrophilic reactant to add to carbon-carbon double bonds;
D. when the electrophilic reactant employed in step C is a hydrolyzable electrophilic compound containing reactive hydrogen, hydrolyzing the product of step C to form alcohols;
E. converting the alcohols to alkyl xanthates; and
F. cracking the product of step E to produce a mixture of n-hexenes containing 1-hexene.

10. A process for making 1-hexene comprising:
A. metathesizing 1-butene to a mixture comprising 3-hexene and ethylene;
B. separating the 3-hexene from the product of step A;
C. reacting the 3-hexene with an electrophilic reactant selected from the group consisting of water and a hydrolyzable electrophilic compound containing reactive hydrogen under acid catalyzed conditions which permit the electrophilic reactant to add to carbon-carbon double bonds;
D. when the electrophilic reactant employed in step C is a hydrolyzable electrophilic compound containing reactive hydrogen, hydrolyzing the product of step C to form alcohols;
E. converting the alcohols produced to alkyl xanthates;
F. separating the 2-xanthate from the product of step E; and
G. cracking the 2-xanthate to produce a mixture of n-hexenes containing 1-hexene.

11. The process of claim 9 or 10 wherein the electrophilic reactant in step C is selected from water, sulfuric acid, and carboxylic acids.

12. The process of claim 9 or 10 further comprising separating the 1-hexene from the product of the cracking step and recycling the remainder of said product to form a portion of the material used to react with the electrophilic reactant.

13. The process of claim 1, 2, 3, 4, 5, 6 or 7 wherein the cracking is conducted in the presence of a mildly basic metal oxide catalyst capable of selectively producing α-olefins.

14. A process for making 1-hexene comprising:
A. metathesizing 1-butene to a mixture comprising 3-hexene and ethylene;
B. separating the 3-hexene from the product of step A;
C. reacting the 3-hexene with an electrophilic compound containing reactive hydrogen under conditions which permit the electrophilic compound containing reactive hydrogen to add to carbon-carbon double bonds;
D. cracking the product of step C to produce a mixture of 2-hexene and 3-hexene;
E. reacting the mixture of 2-hexene and 3-hexene produced in step D with an electrophilic compound containing reactive hydrogen under conditions which permit the electrophilic compound containing reactive hydrogen to add to carbon-carbon double bonds; and
F. cracking the product of step E to produce a mixture of n-hexenes containing 1-hexene.

15. A process for making 1-hexene comprising:
A. metathesizing 1-butene to a mixture comprising 3-hexene and ethylene;
B. separating the 3-hexene from the product of step A;
C. reacting the 3-hexene with an electrophilic compound containing reactive hydrogen under conditions which permit the electrophilic compound containing reactive hydrogen to add to carbon-carbon double bonds;
D. cracking the product of step C to produce a mixture of 2-hexene and 3-hexene;
E. reacting the mixture of 2-hexene and 3-hexene produced in step D with an electrophilic compound containing reactive hydrogen under conditions which permit the electrophilic compound containing reactive hydrogen to add to carbon-carbon double bonds;
F. separating the 2-isomer produced in step E from the product of step E; and
G. cracking said 2-isomer to produce a mixture of n-hexenes containing 1-hexene.

16. The process of claim 14 or 15 wherein the electrophilic compound is selected from the group consisting of water and carboxylic acids.

17. The process of claim 14 or 15 further comprising separating the 1-hexene from the product of the second cracking step and recycling the remainder of said product to form a portion of the material used to react with the electrophilic compound containing reactive hydrogen in step C.

18. The process of claim 14 or 15 wherein the cracking is conducted in the presence of a mildly basic metal oxide catalyst capable of selectively producing α-olefins.

* * * * *